(12) United States Patent
Christensen

(10) Patent No.: US 11,278,248 B2
(45) Date of Patent: Mar. 22, 2022

(54) OCT IMAGING CATHETER WITH LAG CORRECTION

(71) Applicant: AVINGER, INC., Redwood City, CA (US)

(72) Inventor: Bjarne B. Christensen, Sunnyvale, CA (US)

(73) Assignee: Avinger, Inc., Redwood City, CA (US)

( * ) Notice: Subject to any disclaimer, the term of this patent is extended or adjusted under 35 U.S.C. 154(b) by 717 days.

(21) Appl. No.: 16/069,545

(22) PCT Filed: Jan. 25, 2017

(86) PCT No.: PCT/US2017/014921
§ 371 (c)(1),
(2) Date: Jul. 12, 2018

(87) PCT Pub. No.: WO2017/132247
PCT Pub. Date: Aug. 3, 2017

(65) Prior Publication Data
US 2019/0021679 A1    Jan. 24, 2019

Related U.S. Application Data

(60) Provisional application No. 62/286,918, filed on Jan. 25, 2016.

(51) Int. Cl.
*A61B 5/00* (2006.01)
*A61B 17/3207* (2006.01)
(Continued)

(52) U.S. Cl.
CPC .......... *A61B 5/7445* (2013.01); *A61B 5/0036* (2018.08); *A61B 5/0044* (2013.01);
(Continued)

(58) Field of Classification Search
CPC ..... A61B 17/00; A61B 17/22; A61B 17/3207; A61B 17/320758; A61B 17/320783;
(Continued)

(56) References Cited

U.S. PATENT DOCUMENTS 3,367,727 A    2/1968   Ward et al.
3,908,637 A    9/1975   Doroshow
(Continued)

FOREIGN PATENT DOCUMENTS

CN    1875242 A    12/2006
CN    1947652 A    4/2007
(Continued)

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.
(Continued)

*Primary Examiner* — Amelie R Davis
(74) *Attorney, Agent, or Firm* — Shay Glenn LLP

(57) ABSTRACT

A catheter system includes a catheter body, an imaging sensor, a drive motor, a current sensor, a display, and a controller. The catheter body includes a drive shaft. The imaging sensor is fixed relative to the distal end of the driveshaft and is configured to rotate therewith. The drive motor is configured to rotate the drive shaft. The current sensor is configured to measure an amount of current drawn by the drive motor as the drive shaft is rotated. The display is configured to display one or more images obtained by the imaging sensor as the imaging sensor is rotated. The controller is configured to adjust a rotational orientation of the one or more images displayed by the display based upon the measured current.

22 Claims, 9 Drawing Sheets

(51) Int. Cl.
  *A61B 17/22* (2006.01)
  *A61B 17/00* (2006.01)
  *A61B 5/02* (2006.01)
  *A61B 90/00* (2016.01)
  *A61B 17/32* (2006.01)

(52) U.S. Cl.
  CPC .......... *A61B 5/0066* (2013.01); *A61B 5/0084* (2013.01); *A61B 5/02007* (2013.01); *A61B 5/6852* (2013.01); *A61B 17/00* (2013.01); *A61B 17/22* (2013.01); *A61B 17/3207* (2013.01); *A61B 17/320758* (2013.01); *A61B 17/320783* (2013.01); *A61B 2017/00039* (2013.01); *A61B 2017/00061* (2013.01); *A61B 2017/00398* (2013.01); *A61B 2017/320008* (2013.01); *A61B 2017/320791* (2013.01); *A61B 2090/3735* (2016.02); *A61B 2505/05* (2013.01); *A61B 2560/0223* (2013.01); *A61B 2576/00* (2013.01); *A61B 2576/023* (2013.01)

(58) Field of Classification Search
  CPC .......... A61B 2017/00039; A61B 2017/00061; A61B 2017/00398; A61B 2017/320008; A61B 2017/320791; A61B 2090/3735; A61B 2505/05; A61B 2560/0223; A61B 2576/00; A61B 2576/023; A61B 5/0036; A61B 5/0044; A61B 5/0066; A61B 5/0084; A61B 5/02007; A61B 5/6852; A61B 5/7445
  See application file for complete search history.

(56) References Cited

U.S. PATENT DOCUMENTS

| | | | |
|---|---|---|---|
| 4,178,935 | A | 12/1979 | Gekhaman et al. |
| 4,487,206 | A | 12/1984 | Aagard |
| 4,527,553 | A | 7/1985 | Upsher |
| 4,552,554 | A | 11/1985 | Gould et al. |
| 4,578,061 | A | 3/1986 | Lemelson |
| 4,611,600 | A | 9/1986 | Cohen |
| 4,621,353 | A | 11/1986 | Hazel et al. |
| 4,639,091 | A | 1/1987 | Huignard et al. |
| 4,651,753 | A | 3/1987 | Lifton |
| 4,654,024 | A | 3/1987 | Crittenden et al. |
| 4,681,106 | A | 7/1987 | Kensey et al. |
| 4,686,982 | A | 8/1987 | Nash |
| 4,691,708 | A | 9/1987 | Kane |
| 4,729,763 | A | 3/1988 | Henrie |
| 4,771,774 | A | 9/1988 | Simpson et al. |
| 4,781,186 | A | 11/1988 | Simpson et al. |
| 4,841,977 | A | 6/1989 | Griffith et al. |
| 4,857,046 | A | 8/1989 | Stevens et al. |
| 4,920,961 | A | 5/1990 | Grossi et al. |
| 4,926,858 | A | 5/1990 | Gifford, III et al. |
| 5,000,185 | A | 3/1991 | Yock |
| 5,018,529 | A | 5/1991 | Tenerz et al. |
| 5,041,082 | A | 8/1991 | Shiber |
| 5,047,040 | A | 9/1991 | Simpson et al. |
| 5,085,662 | A | 2/1992 | Willard |
| 5,099,850 | A | 3/1992 | Matsui et al. |
| 5,178,153 | A | 1/1993 | Einzig |
| 5,182,291 | A | 1/1993 | Gubin et al. |
| 5,190,050 | A | 3/1993 | Nitzsche |
| 5,192,291 | A | 3/1993 | Pannek, Jr. |
| 5,312,415 | A | 5/1994 | Palermo |
| 5,312,425 | A | 5/1994 | Evans et al. |
| 5,321,501 | A | 6/1994 | Swanson et al. |
| 5,333,142 | A | 7/1994 | Scheps |
| 5,358,472 | A | 10/1994 | Vance et al. |
| 5,366,464 | A | 11/1994 | Belknap |
| 5,372,601 | A | 12/1994 | Lary |
| 5,383,460 | A | 1/1995 | Jang et al. |
| 5,383,467 | A | 1/1995 | Auer et al. |
| 5,425,273 | A | 6/1995 | Chevalier |
| 5,429,136 | A | 7/1995 | Milo et al. |
| 5,431,673 | A | 7/1995 | Summers et al. |
| 5,437,284 | A | 8/1995 | Trimble |
| 5,459,570 | A | 10/1995 | Swanson et al. |
| 5,460,168 | A | 10/1995 | Masubuchi et al. |
| 5,465,147 | A | 11/1995 | Swanson |
| 5,507,760 | A | 4/1996 | Wynne et al. |
| 5,507,795 | A | 4/1996 | Chiang et al. |
| 5,517,998 | A | 5/1996 | Madison |
| 5,556,405 | A | 9/1996 | Lary |
| 5,607,394 | A | 3/1997 | Andersen et al. |
| 5,620,426 | A | 4/1997 | Braithwaite |
| 5,632,754 | A | 5/1997 | Farley et al. |
| 5,632,755 | A | 5/1997 | Nordgren et al. |
| 5,674,232 | A | 10/1997 | Halliburton |
| 5,681,336 | A | 10/1997 | Clement et al. |
| 5,690,634 | A | 11/1997 | Muller et al. |
| 5,722,403 | A | 3/1998 | McGee et al. |
| 5,728,148 | A | 3/1998 | Bostrom et al. |
| 5,749,846 | A | 5/1998 | Edwards et al. |
| 5,795,295 | A | 8/1998 | Hellmuth et al. |
| 5,807,339 | A | 9/1998 | Bostrom et al. |
| 5,830,145 | A | 11/1998 | Tenhoff |
| 5,836,957 | A | 11/1998 | Schulz et al. |
| 5,843,050 | A | 12/1998 | Jones et al. |
| 5,843,103 | A | 12/1998 | Wulfman |
| 5,851,212 | A | 12/1998 | Zirps et al. |
| 5,868,778 | A | 2/1999 | Gershony et al. |
| 5,872,879 | A | 2/1999 | Hamm |
| 5,904,651 | A | 5/1999 | Swanson et al. |
| 5,907,425 | A | 5/1999 | Dickensheets et al. |
| 5,935,075 | A | 8/1999 | Casscells et al. |
| 5,938,602 | A | 8/1999 | Lloyd |
| 5,938,671 | A | 8/1999 | Katoh et al. |
| 5,951,482 | A | 9/1999 | Winston et al. |
| 5,951,581 | A | 9/1999 | Saadat et al. |
| 5,951,583 | A | 9/1999 | Jensen et al. |
| 5,956,355 | A | 9/1999 | Swanson et al. |
| 5,957,952 | A | 9/1999 | Gershony et al. |
| 5,987,995 | A | 11/1999 | Sawatari et al. |
| 5,997,558 | A | 12/1999 | Nash |
| 6,001,112 | A | 12/1999 | Taylor |
| 6,007,530 | A | 12/1999 | Dornhofer et al. |
| 6,010,449 | A | 1/2000 | Selmon et al. |
| 6,013,072 | A | 1/2000 | Winston et al. |
| 6,017,359 | A | 1/2000 | Gershony et al. |
| 6,027,514 | A | 2/2000 | Stine et al. |
| 6,032,673 | A | 3/2000 | Savage et al. |
| 6,048,349 | A | 4/2000 | Winston et al. |
| 6,080,170 | A | 6/2000 | Nash et al. |
| 6,106,515 | A | 8/2000 | Winston et al. |
| 6,110,164 | A | 8/2000 | Vidlund |
| 6,120,515 | A | 9/2000 | Rogers et al. |
| 6,120,516 | A | 9/2000 | Selmon et al. |
| 6,134,002 | A | 10/2000 | Stimson et al. |
| 6,134,003 | A | 10/2000 | Tearney et al. |
| 6,152,938 | A | 11/2000 | Curry |
| 6,152,951 | A | 11/2000 | Hashimoto et al. |
| 6,160,826 | A | 12/2000 | Swanson et al. |
| 6,175,669 | B1 | 1/2001 | Colston et al. |
| 6,176,871 | B1 | 1/2001 | Pathak et al. |
| 6,183,432 | B1 | 2/2001 | Milo |
| 6,193,676 | B1 | 2/2001 | Winston et al. |
| 6,206,898 | B1 | 3/2001 | Honeycutt et al. |
| 6,228,076 | B1 | 5/2001 | Winston et al. |
| 6,241,744 | B1 | 6/2001 | Imran et al. |
| 6,283,957 | B1 | 9/2001 | Hashimoto et al. |
| 6,285,903 | B1 | 9/2001 | Rosenthal et al. |
| 6,290,668 | B1 | 9/2001 | Gregory et al. |
| 6,294,775 | B1 | 9/2001 | Seibel et al. |
| 6,299,622 | B1 | 10/2001 | Snow et al. |
| 6,307,985 | B1 | 10/2001 | Murakami et al. |
| 6,375,615 | B1 | 4/2002 | Flaherty et al. |
| 6,402,719 | B1 | 6/2002 | Ponzi et al. |
| 6,416,527 | B1 | 7/2002 | Berg et al. |
| 6,445,939 | B1 | 9/2002 | Swanson et al. |
| 6,445,944 | B1 | 9/2002 | Ostrovsky |

(56) References Cited

U.S. PATENT DOCUMENTS

| | | |
|---|---|---|
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,213,224 B2 | 2/2019 | Guggenheimer et al. |
| 10,314,667 B2 | 6/2019 | Garvey et al. |
| 10,406,316 B2 | 9/2019 | Garvey et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashir et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |

(56) References Cited

U.S. PATENT DOCUMENTS

| | | |
|---|---|---|
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unai et al. |
| 2007/0196926 A1 | 8/2007 | Soito et al. |
| 2007/0213618 A1* | 9/2007 | Li ................. A61B 1/00183 600/476 |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |

(56) References Cited

U.S. PATENT DOCUMENTS

| | | |
|---|---|---|
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1* | 3/2011 | Hastings .............. A61B 8/4461 600/467 |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0035692 A1 | 2/2013 | Sorensen et al. |
| 2013/0072787 A1 | 3/2013 | Wallace et al. |
| 2013/0096589 A1 | 4/2013 | Spencer et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1 | 5/2015 | Gupta et al. |
| 2015/0146211 A1 | 5/2015 | Bhagavatula et al. |
| 2015/0164530 A1 | 6/2015 | Carver et al. |
| 2015/0208922 A1 | 7/2015 | Simpson et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |
| 2016/0262791 A1 | 9/2016 | Patel et al. |
| 2016/0262839 A1 | 9/2016 | Spencer et al. |
| 2016/0310700 A1 | 10/2016 | Drake et al. |
| 2016/0338582 A1 | 11/2016 | Tachibana et al. |
| 2016/0354109 A1 | 12/2016 | Guggenheimer et al. |
| 2016/0354110 A1 | 12/2016 | Guggenheimer et al. |
| 2017/0065295 A1 | 3/2017 | Patel et al. |
| 2017/0172666 A1 | 6/2017 | Govari et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0049700 A1 | 2/2018 | Black et al. |
| 2018/0146978 A1 | 5/2018 | Patel et al. |
| 2018/0192880 A1 | 7/2018 | Patel et al. |
| 2018/0200488 A1 | 7/2018 | Drake et al. |
| 2018/0207417 A1 | 7/2018 | Zung et al. |
| 2018/0256039 A1 | 9/2018 | Smith et al. |
| 2018/0256187 A1 | 9/2018 | Patel et al. |
| 2018/0364024 A1 | 12/2018 | Baca et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |

(56) References Cited

FOREIGN PATENT DOCUMENTS

| | | |
|---|---|---|
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2017/007853 A1 | 1/2017 |
| WO | WO2017/132247 A1 | 8/2017 |
| WO | WO2018/094041 A1 | 5/2018 |

OTHER PUBLICATIONS

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Newhauser et al.; U.S. Appl. No. 15/954,407 entitled "Occlusion-crossing devices," filed Apr. 16, 2018.

Patel et al.; U.S. Appl. No. 16/490,903 entitled "Atherctomy catheter," filed Jul. 2, 2019.

Black et al.; U.S. Appl. No. 16/506,851 entitled "Optical coherence tomography for biologicai imaging," filed Jul. 9, 2019.

Patel et al.; U.S. Appl. No. 16/516,093 entitled "High speed chronic total occlusion crossing devices," filed Jul. 18, 2019.

Smith et al.; U.S. Appl. No. 16/941,310 entitled "Chronic total occlusion crossing devices with imaging," filed Jul. 28, 2020.

Spencer et al.; U.S. Appl. No. 16/943,446 entitled "Catheter-based off-axis optical coherence tomography imaging system," filed Jul. 30, 2020.

Schmitt et al.; A new rotational thrombectomy catheter: System design and first clinical esperiences; Cardiovascular and Interventional Radiology; Sprinver-Verlag; 22(6); pp. 504-509; Nov. 1, 1999.

Patel et al.; U.S. Appl. No. 16/801,047 entitled "Micro-molded anamorphic reflector lens for image guided therapeutic/diagnostic catheters," filed Feb. 25, 2020.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Leitgeb et al.; Performance of fourier domain vs time domain optical coherence tomography; Optics Express; 11(8); pp. 889-894; Apr. 21, 2003.

Rollins et al.; Optimal interferometer designs for optical coherence tomography; Optics Letters; 24(21); pp. 1484-1486; Nov. 1999.

Tachibana et al.; U.S. Appl. No. 16/372,112 entitled "Atherectomy catheter drive assemblies," filed Apr. 1, 2019.

Radjabi et al.; U.S. Appl. No. 16/347,840 entitled "Methods, systems and apparatuses for displaying real-time catheter position," filed May 7, 2019.

Patel et al.; U.S. Appl. No. 17/046,066 entitled "Occlusion-crossing devices," filed Oct. 8, 2020.

Simpson et al.; U.S. Appl. No. 17/075,548 entitled "Identification of elastic lamina to guide interventional therapy," filed Oct. 20, 2020.

Sharma et al.; Common-path optical coherence tomography with side-viewing bare fiber probe for endoscopic optical coherence tomography; vol. 78; 113102; 5 pages; Nov. 6, 2007.

Rosenthal et al.; U.S. Appl. No. 16/105,743 entitled "Atherectomy catheter with laterally-displaceable tip," filed Aug. 20, 2018.

Patel et al.; U.S. Appl. No. 16/148,246 entitled "Atherectomy catheter with serrated cutter," filed Oct. 1, 2018.

Simpson et al.; U.S. Appl. No. 16/194,183 entitled "Indetification of elastic lamina to guide interventional therapy," filed Nov. 16, 2018.

Fernandez et al., U.S. Appl. No. 16/305,136 entitled "Catheter device with detachable distal end," filed Nov. 28, 2018.

Patel et al., U.S. Appl. No. 16/310,470 entitled "Atherectomy catheter with shapeable distal tip," filed Dec. 17, 2019.

Stamper et al.; Plaque characterization with optical coherence tomography, Journal of the American College of Cardiology. 47(8); pp. 69-79; Apr. 18, 2006.

Patel et al.; U.S. Appl. No. 16/681,807 entitled "Atherectomy catheters and occlusion crossing devices," filed Nov. 12, 2019.

Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vemelle.noel/Plastic_Snap_fit_design.pdf) on Sep. 26, 2018.

(56) References Cited

OTHER PUBLICATIONS

Merriam Webster; Proximal (Definition); 10 pages; retrieved from the internet (https://www.merriam-webster.com/dictionary/proximal) on Jun. 9, 2021.
WIKIPEDIA; Hinge; 4 pages; retrieved from the internet (https://en.wikipedia.org/w/index.php?title=Hinge&oldid=479569345) on Jun. 9, 2021.
Smith et al.; U.S. Appl. No. 17/189,123 entitled "Optical pressure sensor assembly," filed Mar. 1, 2021.
Kankaria, U.S. Appl. No. 17/209,162 entitled "Optical coherence tomography with graded index fiber for biological imaging," filed Mar. 22, 2021.
Newhauser et al.; U.S. Appl. No. 17/209,168 entitled "Occlusion-crossing devices," filed Mar. 22, 2021.
Patel et al.; U.S. Appl. No. 17/347,419 entitled "Micro-molded anamorphic reflector lens for image guided therapeutic/diagnostic catheters," filed Jun. 14, 2021.

\* cited by examiner

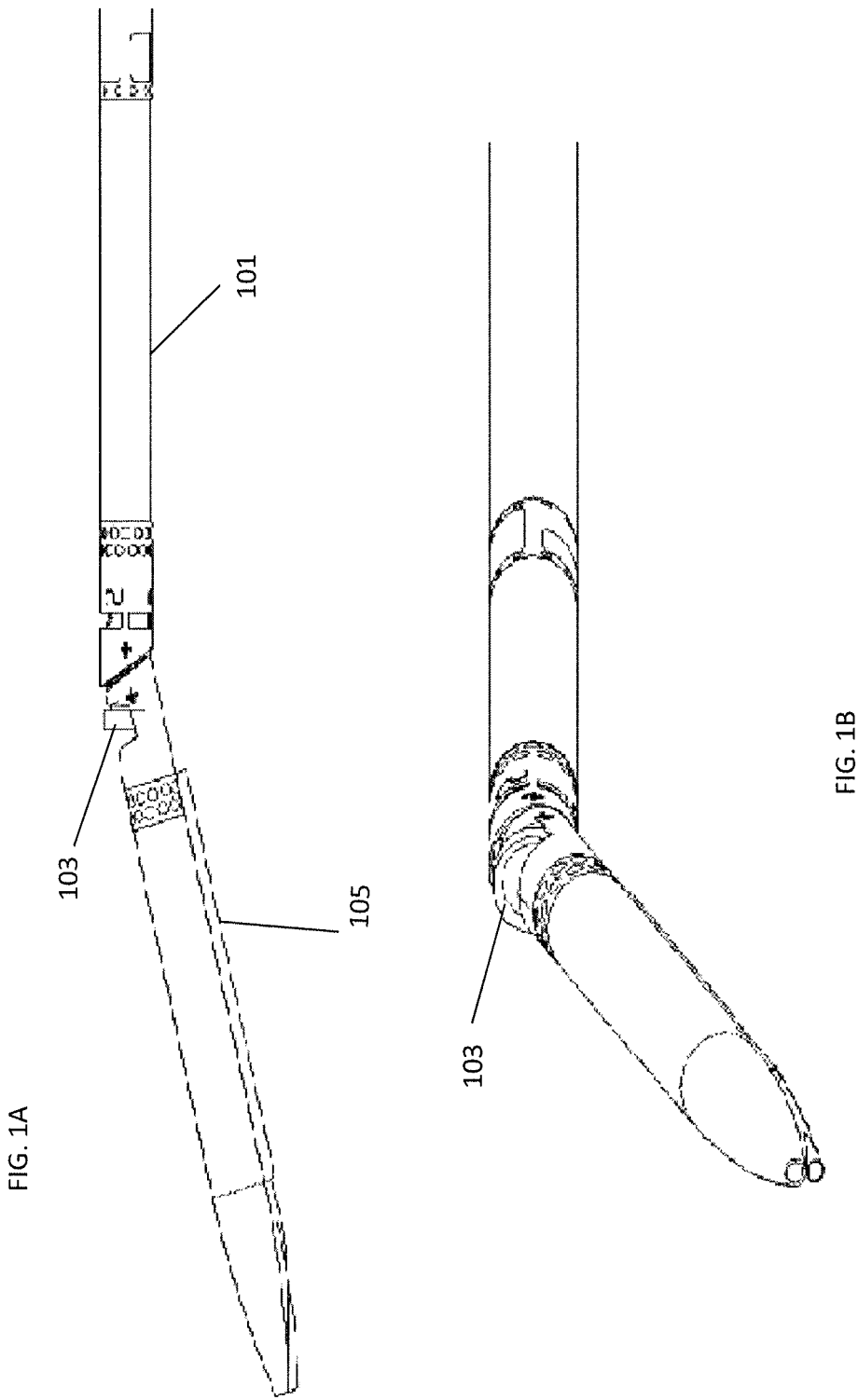

OCT IMAGING CATHETER WITH LAG CORRECTION

CROSS REFERENCE TO RELATED APPLICATIONS

This application claims priority to U.S. Provisional Patent Application No. 62/286,918, filed Jan. 25, 2016, titled "OCT IMAGING CATHETER WITH LAG CORRECTION", which is herein incorporated by reference in its entirety.

This application may be related to PCT Patent Application No. PCT/US2015/014613, filed Feb. 5, 2015, titled, "ATHERECTOMY CATHETERS AND OCCLUSION CROSSING DEVICES", Publication No. WO2015/120146A1, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are image correction systems that can be coupled to imaging catheters. More specifically, imaging correction systems and related methods that correct for rotational distortions experienced by imaging catheters are described.

BACKGROUND

Atherectomy is a minimally invasive endovascular surgery technique that removes atherosclerosis (plaque buildup in the blood vessels). By removing the majority of plaque mass (debulking), atherectomy creates a larger internal lumen and dramatically increases the compliance of the arterial wall. As a result, stent deployment is greatly enhanced.

Additionally, atherectomy provides several advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By using atherectomy to remove the disease with minimal force applied to the vessel, large gains in lumen size can be created with decreased vessel wall injury and limited elastic recoiling. These effects have been shown to generate better acute results and lower restenosis rates.

Atherectomy devices can be accompanied by image guidance, such as optical coherence tomography (OCT). Having imaging capabilities provide for safer and more targeted treatment. Image guidance is particularly useful in showing the operator where plaque masses are located and to focus debulking where the plaque is visualized, greatly decreasing the risk associated with atherectomy. One additional benefit of having an accompanying visualization system is that the catheter operator does not have to treat the lesions or plaque as being all concentric in nature, when in fact, the majority of the lesions and plaque found are eccentric. This circumferential approximation approach to removing lesions and plaque may not fully remove plaque from one region and potentially cut or stretch healthy vessel. Thus, the ability to visualize the plaque or lesions in the vessel will allow the operator to debulk only in the required areas while leaving healthy tissue untouched.

While having an imaging system coupled to the atherectomy catheter allows for safer procedure than without, on-board imaging can have inaccuracies. For example, placement of the imaging sensor may affect accuracy. That is, imaging elements positioned at or closer to the distal end of the atherectomy catheter can experience greater bending or torque than is experienced at the proximal end. Further, if the imaging element is positioned on or proximate to the cutting element, then when the cutting portion experiences resistance from plaque buildup in the vessel or from the curvature of the vessel itself, deviations can occur in the image. Similarly, a catheter moving through a body cavity or lumen may also experience torque depending on the body lumen and the environment within that body lumen, which can cause distortions in the images.

Additionally, rotational distortions can occur as a result of the cutter turning more slowly than the motor at the proximal end, the cutter vibrating, or the cutter jumping when encountering tissue of different characteristics. These various deviations in the images can be caused by what is called "rotational lag," i.e., a lag between the rotation that the user may or may not have intentionally applied to the catheter and the actual and potentially unintentional rotation of the imaging sensor at the distal end of the catheter. Such rotational lag can be enhanced in some catheters, as the rotational position of the displayed image may be fixed in some catheters according to an index position relative to the catheter motor rather than the distal end of the catheter. Accordingly, there is a need for an imaging atherectomy catheter that accounts or adjusts for rotational lag.

One method previously disclosed for adjusting images distorted by rotational lag was to manually rotate the catheter to compensate for the lag between the rotation applied by the user at the proximal end and the actual rotation of the distal end of the catheter. However, this method does not provide a consistent way of compensating for the rotational lag experienced, as manual adjustment of the catheter will likely differ from user to user as well as in response the uniquely different resistance experienced in different body lumen. Another method previously disclosed for dealing with rotational lag was to separate the images into both a depth versus time image, called a waterfall image, and an azimuthal image that contains angular rotation information. While this method allows the user to see both types of images (showing both azimuthal and time versus depth information), it is not an intuitive way to view the interior of a vessel.

Thus, it would be advantageous to have an atherectomy catheter system with imaging that is able to adjust for rotational lag instantaneously and dynamically. Furthermore, it would also be more cost-effective and accurate to implement a system for correcting rotational lag that utilizes a simple measurement of existing condition to determine if correction is needed. Having a simple measurement that correlates to rotational lag prior to an image being taken would remove the need for having applications and programs to calculate and adjust the image at the output end.

SUMMARY OF THE DISCLOSURE

In general, in one embodiment, a catheter system includes a catheter body, an imaging sensor, a drive motor, a current sensor, a display, and a controller. The catheter body includes a drive shaft. The imaging sensor is fixed relative to the distal end of the driveshaft and is configured to rotate therewith. The drive motor is configured to rotate the drive shaft. The current sensor is configured to measure an amount of current drawn by the drive motor as the drive shaft is rotated. The display is configured to display one or more images obtained by the imaging sensor as the imaging sensor is rotated. The controller is configured to adjust a rotational orientation of the one or more images displayed by the display based upon the measured current.

This and other embodiments can include one or more of the following features. The imaging sensor can be an optical coherence tomography (OCT) imaging sensor. The catheter body can further include a cutter configured to rotate with the driveshaft. The imaging sensor can be attached to the cutter. The catheter system can further include a nosecone attached to the distal end of the catheter body and configured to pivot relative thereto. The sensor can be a current sense resistor. The one or more images can be displayed on the display as a sector view. The controller can be configured adjust a rotational orientation of the one or more images by delaying projection of the one or more images on the display based upon the measured current. The controller can be further configured to adjust a rotational orientation of the one or more images based upon a predetermined reference current value and gain value. The controller, drive motor, and sensor can be part of a drive assembly configured to drive the catheter.

In general, in one embodiment, a catheter drive assembly includes a drive motor, a sensor, and a controller. The drive motor is configured to rotate a drive shaft and imaging sensor of a catheter at first index pulse. The sensor is configured to measure an amount of current drawn by the drive motor as the drive shaft is rotated at the first index pulse. The controller is configured to determine a second index pulse based upon the measured current and the first index pulse and send the second index pulse to a display so as to allow display of images gathered by the imaging sensor that are adjusted for rotational lag. The second index pulse is delayed relative to the first index pulse.

This and other embodiments can include one or more of the following features. The sensor can be a current sense resistor. The controller can be configured to determine a second index pulse further based upon a predetermined reference current value and gain value. The imaging sensor can be an optical coherence tomography (OCT) imaging sensor.

In general, in one embodiment, a method of correcting for rotational lag includes: obtaining a reference current value for an imaging catheter when there is no torque on a driveshaft of the catheter; measuring an amount of current delivered to a drive motor to rotate the driveshaft during a procedure; determining that there has been rotational lag of the driveshaft by determining that the measured amount of current is above the reference current value by a determined amount; and correcting a displayed image for the rotational lag based upon the determined amount.

This and other embodiments can include one or more of the following features. The measuring, determining, and correcting steps can be performed during use of the catheter in an atherectomy procedure. Correcting a displayed image for the rotational lag based upon the determined amount can include delaying an index pulse to the displayed image so as to delay projection of the image. The imaging catheter can be an optical coherence tomography (OCT) imaging catheter, and the displayed image can be an OCT image.

In general, in one embodiment, a method of correcting for rotational lag includes: obtaining a correlation between an amount of rotational distortion in an image and an amount of current drawn by a drive motor of an imaging catheter; measuring an amount of current delivered to the drive motor to rotate a driveshaft of the imaging catheter with the drive motor; when the measured current is above a predetermined value, using the correlation to determine a rotational adjustment value; and adjusting an orientation of an image based upon the rotational adjustment value.

This and other embodiments can include one or more of the following features. The measuring, using, and adjusting steps can be performed during use of the catheter in an atherectomy procedure. Adjusting an orientation of an image can include delaying an index pulse to a display so as to delay projection of the image on the display. The imaging catheter can be an optical coherence tomography (OCT) imaging catheter, and the image can be an OCT image.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1D are schematics showing an exemplary atherectomy catheter. FIG. 1A is a side view of the atherectomy catheter. FIG. 1B shows a catheter where the cutter is exposed. FIG. 1C is a second example of an atherectomy catheter. FIG. 1D shows a cross section of the catheter.

DETAILED DESCRIPTION

Described herein are methods and assemblies for addressing rotational lag of an imaging catheter (e.g., an atherectomy catheter) in a simple, cost effective, and dynamic way. The methods and assemblies described herein are configured to determine the existence of rotational lag at the imaging element and dynamically compensate for the lag before the image is recorded and displayed.

The catheters described herein can include an elongate flexible catheter body and a cutting element. In some embodiments, the cutting element can be an annular rotatable cutter configured to rotate to shear tissue away from the vessel wall. In other embodiments, cutting element can include a distal tip having a proximal-facing cutting edge configured to scrape tissue away from the vessel wall. The catheters described herein can further include on-board imaging, such as optical coherence tomography (OCT) imaging. The optical fiber for the OCT imaging can, for example, extend substantially along the longitudinal axis of the catheter body. In some embodiments, the optical fiber can be attached to the rotatable cutter and configured to rotate therewith. In other embodiments, the optical fiber can be attached to a separate imaging shaft.

Figure 1C:
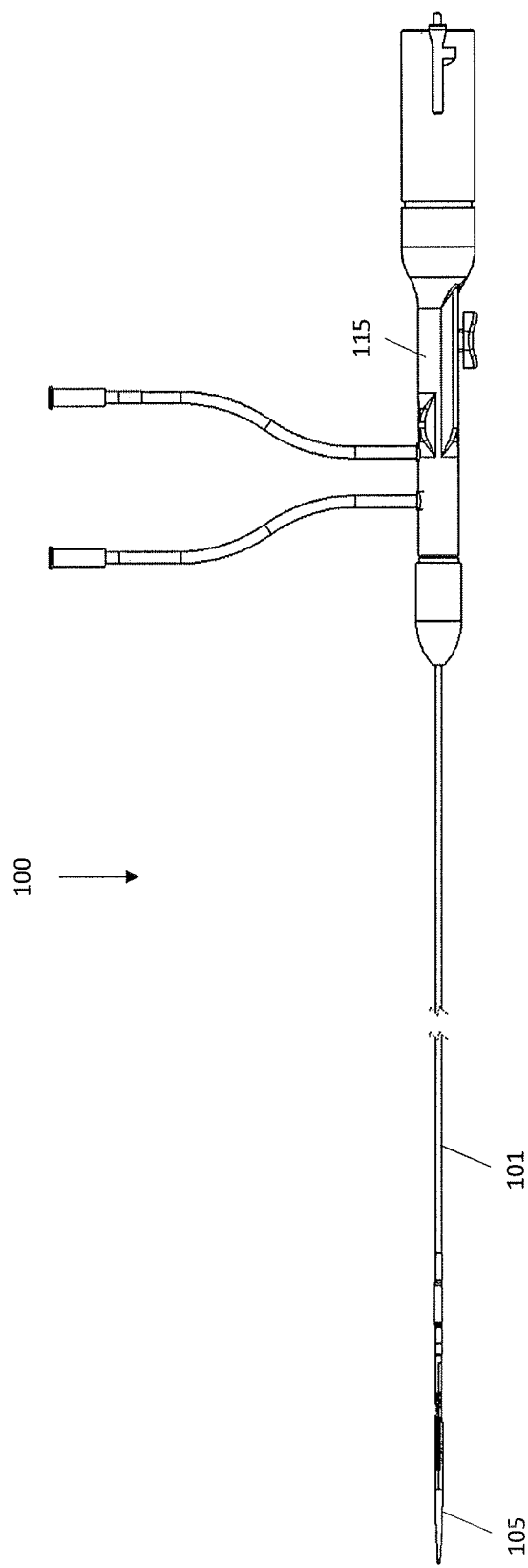
Figure 1D:
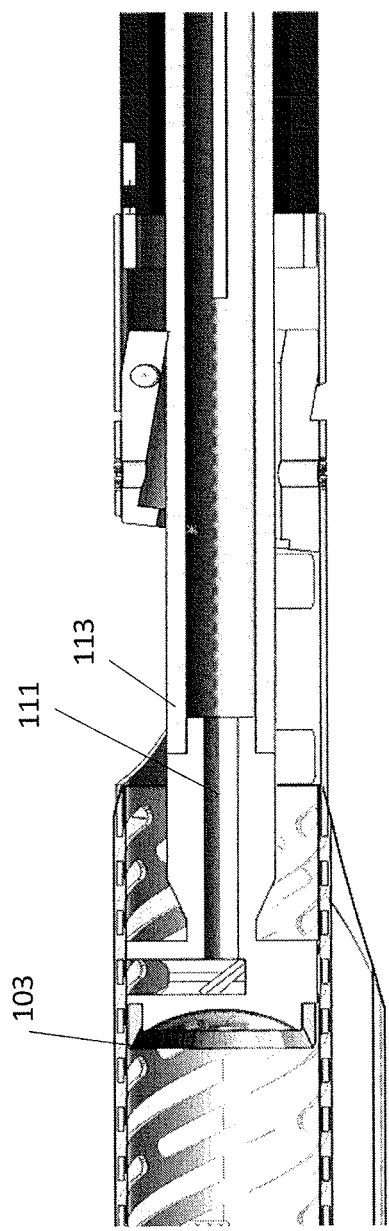

FIGS. 1A-1C show an exemplary atherectomy catheter. Referring to FIG. 1A, the atherectomy catheter 100 can include a catheter body 101, a cutter 103 at a distal end of the catheter body 101 attached to a driveshaft 113, and a nosecone 105 at a distal end of the catheter body 101. The nosecone 105 can further include a cutting window through which the cutting edge of the cutter 103 can be exposed. The nosecone 105 can be configured to deflect away from the longitudinal axis of the catheter body at an angle. In use, this deflection can expose the cutter 103 through the cutting window and/or radially push the cutter 103 into a wall of the vessel in which the atherectomy catheter is inserted. As shown in FIG. 1D, the catheter 100 can further include an on-board imaging system, such as optical coherence tomography (OCT). The optical fiber 111 for the OCT imaging element can run through the center of the driveshaft 113. Further, the optical fiber 111 can be attached to the cutter 103 and be configured to spin therewith.

Further, the catheter 100 may include a handle 115 and/or drive system that includes controls for regulating the displacement, rotation, and/or imaging capabilities of the imaging system. The catheter 100 can be configured to be attached to a control system and/or imaging console for displaying the images gathered with the on-board in imaging system.

Further, the catheter 100 can be configured to work with a control system configured to correct for image distortion, e.g., to correct for rotational lag. Because a catheter is not an ideal torque transmitting entity, there will be some phase delay (θ) for which the distal end of the catheter does not rotate when the proximal end of the catheter is rotated. This phase delay can cause incorrect orientation of the image when the catheter is torqued and/or the direction of rotation changes, called rotational lag. A host of causes may contribute to potential rotational lag. These include torqueing of the catheter due to the tortuosity of the vasculature or force exerted by the operator, cutter position, the type of plaque being excised, and/or any other factors that may apply a torsional load on the catheter.

Figure 2:
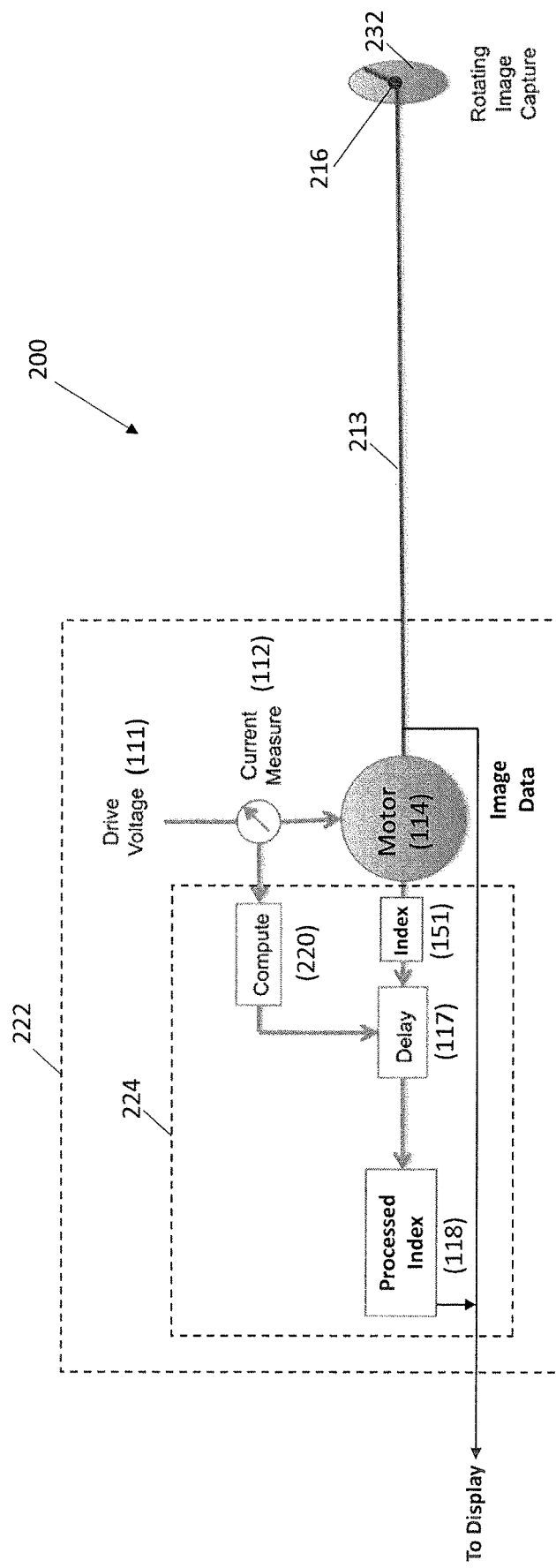
FIG. 2 is a schematic showing a dynamic adjustment to compensate for rotational lag.

FIG. 2 shows a diagram of an atherectomy system 200 configured to correct for rotational lag. The system includes a drive assembly 222, which can be a drive assembly such as those described in U.S. patent application Ser. No. 14/400,151, filed Nov. 10, 2014, titled "ATHERECTOMY CATHETER DRIVE ASSEMBLIES", now U.S. Pat. No. 9,345,398 and PCT Patent Application No. PCT/US2016/041193, filed Jul. 6, 2016, titled "SELF-ALIGNMENT MECHANISM FOR IMAGING CATHETER AND DRIVE ASSEMBLY", Publication No. WO 2017/007853, the entireties of which are incorporated by reference herein. The drive assembly 222 includes a drive shaft motor 114 configured to rotate the drive shaft 213 (and the imaging sensor 216 at the distal end thereof) of the catheter. As the drive shaft motor 114 rotates, it provides an index pulse, which can be read by a controller 224 at (e.g., at 151) every time the motor drive shaft passes a set reference point (e.g., a top dead center position). The drive assembly further includes a drive voltage source 111 to power the drive shaft motor.

In use, the motor 114 can rotate the drive shaft 213 and imaging sensor 216 to gather image data from a circumferential area 232 (e.g., within a body lumen, such as a blood vessel). The image data can be sent back through a controller 224. Simultaneously, the controller 224 can determine the index pulse 151 of the motor 114. The imaging data can then be sent to the display with a set timestamp based upon the index, e.g., such that the top of the displayed OCT image corresponds to the top dead center position on the drive shaft. As torque is applied to the driveshaft 213, however, the displayed image will be rotationally misaligned (or delayed) relative to the actual position of the sensor 216 if a delay is not added to the index pulse.

As such, a current sensor 112 can be disposed between the drive voltage source 111 and the drive shaft motor 114 for continuous monitoring of the current drawn by the drive shaft motor 114. In some variations, the current is sensor can be integral with the motor 114. In other variations, the current sensor 112 can be a current sensor resistor placed in series with the drive shaft motor 114. The instantaneous current of the motor 114 will vary as a function of the torsional load, meaning that the current drawn will change as a function of the torsional strain the catheter experiences. By measuring the instantaneous current of the motor 114, the torsional load on the motor 114 may be estimated.

The controller 224 can be configured to correlate the amount of torque load experienced at the distal end of the catheter (i.e., at the imaging sensor 216) to the change in current drawn from the drive motor 114 (i.e., to compute the rotational lag). Based upon the rotational lag, the controller 224 can implement a delay 117 in the index pulse. The delay 117 can result in a new processed index 118. This processed index 118 instructs the display to delay the presentation of the data in the OCT image by a set time in order to rotationally align the image with the original reference orientation (e.g., place the image back in the top dead center position).

In some embodiments, the method of correcting for rotational lag can include two separate steps: (1) calibrating the system to determine the additional motor current draw relative to torsional load; and (2) then determining the instantaneous motor current of the system during use and making a correction in the resulting image.

In some embodiments, the first step can be performed largely empirical, i.e., one or more different models of catheters can be repeatedly tested in order to obtain a correlation between the change in current and the amount of rotational distortion experienced by that particular model of catheter. In some embodiments, two important parameters, the offset value and the gain value, can be calculated for any given catheter model and then used to determine the correct correlation between the current and amount of rotational distortion. The offset value corresponds to an amount of current that the drive motor draws when there is no lag. The offset value is thus equivalent to the current that the drive motor draws when the catheter is in a relaxed position with the cutter closed. The gain value is a numeric value that allows correction of the rotational image based upon the difference between the measured current and the offset value.

In some embodiments, the second step can be performed dynamically by a controller. That is, once a particular model of catheter has been calibrated in the first step for torsional resistance as a function of rotational distortion (i.e., once the offset value and gain value have been determined for the model), it is possible to estimate the instantaneous rotational distortion for that particular catheter/catheter model and apply an appropriate amount of correction to the resulting image. Referring back to FIG. 2, doing so can include measuring the instantaneous current with sensor 112. The adjustment for rotational lag can be performed dynamically during the use of the catheter, i.e., without direction or input from the user. As a result, the user can advantageously view an image that truly corresponds to what the optical fiber is detecting at the distal end of the catheter or at the cutting region without undesired rotational distortion of the image.

Steps for Calibrating Catheter

Figure 3:
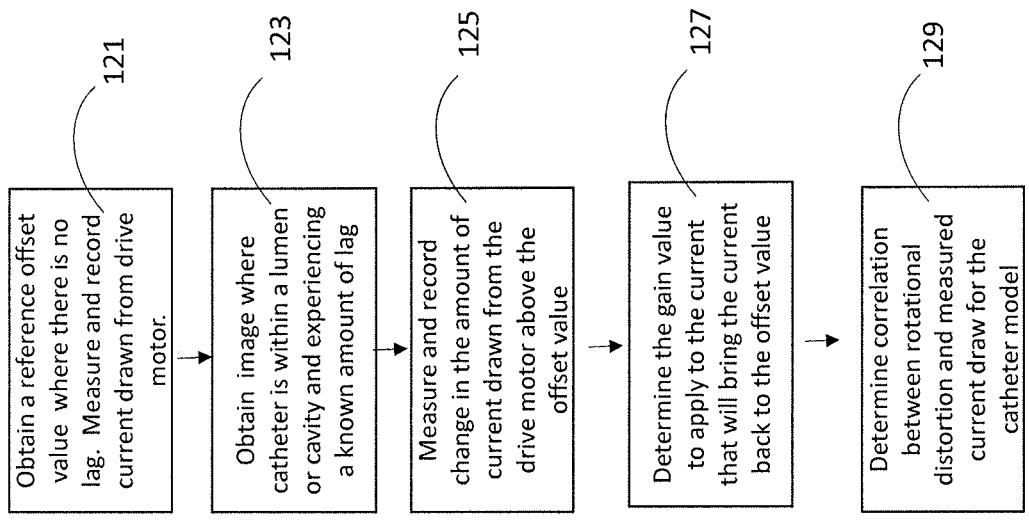
FIG. 3 is a flow chart summarizing the steps in calibrating a catheter.

FIG. 3 is a flowchart detailing exemplary steps for calibrating a particular model of catheter, such as catheter 100, to determine the correlation between the additional motor current drawn by the motor and torsional load. Catheters considered to be a different model can be, for example, those where the driveshafts have different characteristics (e.g., dimensions, spring, etc.) such that the resulting relationship between torsion and current draw will be different. At step 121, a reference current value (called the offset value) is determined. The offset value is the current reading obtained when the catheter is in a relaxed, idle state where the catheter is outside the body cavity and where the cutter is closed. At step 123, an image can be obtained with the imaging sensor while the catheter is in the relaxed and idle state. This idle image can have a particular set orientation or rotational position (e.g., which can be determined based upon markers in the image).

At step 125, an amount of torque can be placed on the driveshaft, such as by opening the nosecone to expose the cutter. Due to the increased torque, the current drawn by the motor will be some amount over the offset. This change in current over the offset value can be measured and recorded. The gain value may then be determined, based upon equation 1 below:

$$R=C(M-O)G \quad \text{(Equation 1)}$$

where R is the radial adjustment value in degrees (i.e., the amount of adjustment required to place the resulting image back at the correct rotational orientation), C is a constant (in degrees/amps), O is the offset value in amps, M is the measured current in amps, and G is the gain value. That is, at this step, the appropriate gain value for the catheter model can be determined so as to rotate the image back to it's original idle position. As shown in Table 1 (which shows experimentally gathered values of offset, gain, and R), the gain value should be the same for a particular catheter model regardless of the value of R. This step can be performed, for example, empirically.

TABLE 1

Experimental Results of Single Model of Catheter

| Catheter Number | Offset | Gain | Clocking degrees (R) |
|---|---|---|---|
| 1 | 400 | 25 | 90 |
| 2 | 400 | 25 | 95 |
| 27 | 400 | 25 | 170 |
| 20 | 400 | 25 | 120 |
| 35 | 400 | 25 | 30 |
| 13 | 400 | 25 | 100 |
| 21 | 400 | 25 | 160 |
| 10 | 400 | 25 | 120 |
| 7 | 400 | 25 | 90 |
| 4 | 400 | 25 | 135 |
| 11 | 400 | 25 | 100 |
| 26 | 400 | 25 | 170 |
| 19 | 400 | 25 | 100 |
| 23 | 400 | 25 | 90 |
| 16 | 400 | 25 | 80 |
| 12 | 400 | 25 | 85 |
| 28 | 400 | 25 | 90 |
| 5 | 400 | 25 | 170 |
| 24 | 400 | 25 | 100 |
| 17 | 400 | 25 | 80 |

In some embodiments, Equation 1 can be considered valid for M greater than or equal to O. If M is less than O, then R (or the radial adjustment) can be considered zero.

Thus, at the calibration step, the offset value and gain values are determined so as to rotate an image back to its original position (i.e., with a known or observed R). At step 129, then, the correlation for the particular catheter can be determined (i.e., C, G, and O can be filled into Equation 1, allowing the rotational adjustment to be determined going forward depending upon the measured current (M).

Using a Catheter Calibrated for Rotational Lag

Figure 4:
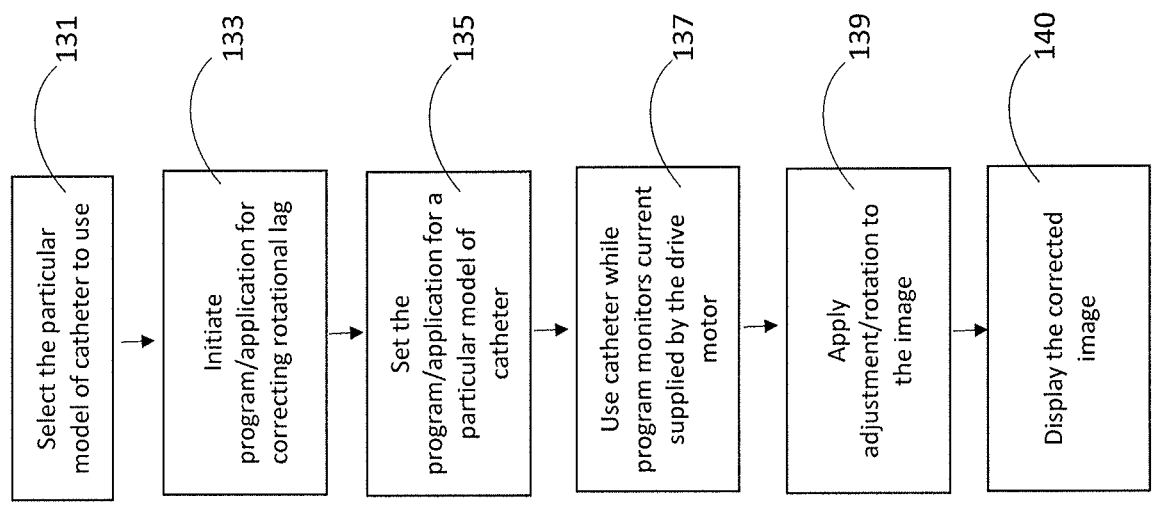
FIG. 4 is a flow chart summarizing the steps of correcting for rotational lag when using an atherectomy catheter.

FIG. 4 is a flow chart showing the steps for dynamically correcting for rotational lag using a calibrated catheter. At step 131, an operator select a particular catheter. At step 133, the operator initiates the program for dynamically and instantaneously correcting for rotational lag. The program can be based upon the determined correlation for the catheter model from step 129 of FIG. 3. As such, the appropriate correlation can be selected at step 135 (e.g., by entering the particular catheter model identification number in the controller). At step 137, the user can operate the catheter (e.g., as part of an atherectomy procedure) while the program monitors the current supplied to the drive motor against the offset current value. At step 139, if the measured current goes above the offset value, then the value R can be obtained (based upon equation 1 and the measured current). Based upon the value R, an amount of adjustment or rotation can be applied to the image to ensure that the image maintains the correct orientation. Once adjusted, the image will be captured and displayed for the user (step 140).

There are a number of ways that the rotational lag may be compensated/adjusted for using the determined radial adjustment value (R). In one example, the image displayed can be delayed. This is based on the observation that the imaging system (e.g., OCT) provides a continuous stream of imaging data as the catheter is in operation. As the imaging element sweeps along with the drive motor, an image is swept out radially. The image displayed shown is the data obtained for that image and as it relates to a reference (e.g., the top-dead center). When rotational lag is present and twists the optical element, there is a misalignment between the top-dead center as it is defined the drive assembly and the image taken at the end of the imaging element. Because there is a delay in the detecting the true image at the end of the imaging element, by intentionally delaying the top-dead center pulse that is sent along with the image date for a set time (based on Equation 1), the image displayed can be aligned with the image detected. In such an embodiment, the time delay may be equated to the radial adjustment value (R) according to Equation 2:

$$T=(R\times60)/(RPM\times360) \quad \text{(Equation 2)}$$

where T is the time in seconds, R is the radial adjustment value, and RPM is the speed of the drive motor in revolutions per minute. Accordingly, the index pulse can be delayed and sent from the drive assembly to the display at the delayed pulse so as to maintain the orientation of the image (i.e., the top dead center position). In some embodiments, the image can be adjusted once per revolution of the driveshaft (i.e., once per input pulse) using the controller in the drive assembly.

The methods and systems for dynamically correcting rotational lag may also include associated software programs, and applications that are able to correlate the amount of change in current from the drive motor or other electrical property and an amount of rotational lag.

Figure 5A:
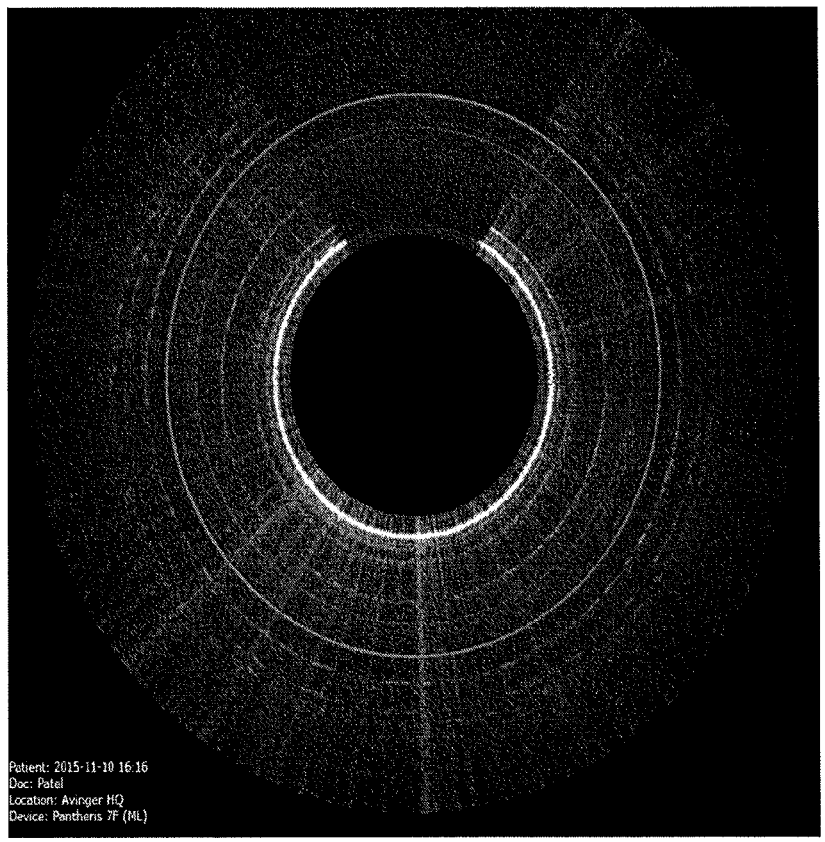
FIG. 5A is an image from an atherectomy catheter as the cutting element is starting to open.
Figure 5B:
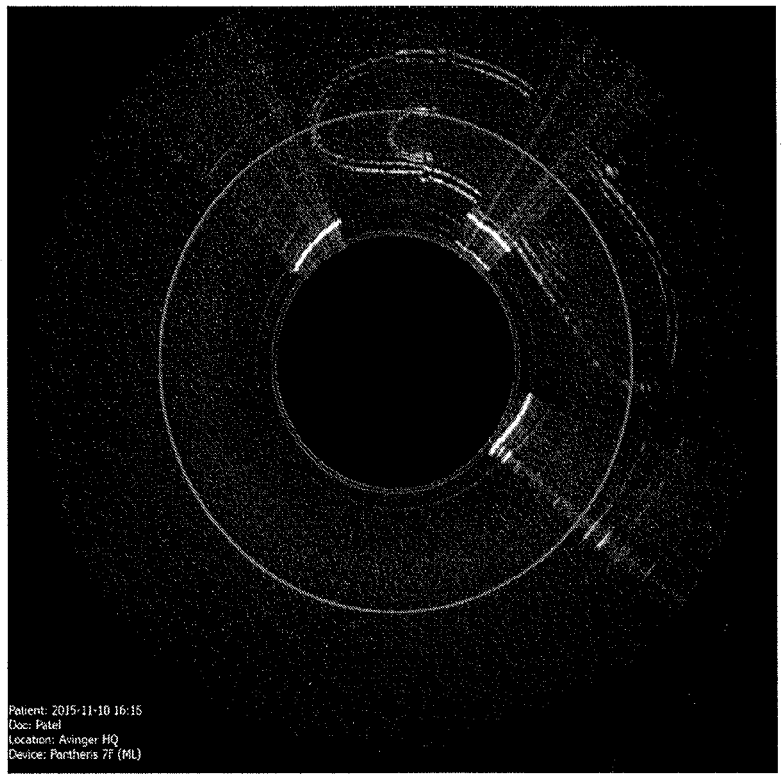
FIG. 5B is an image from an atherectomy catheter that is fully open where there is no dynamic image correction
Figure 5C:
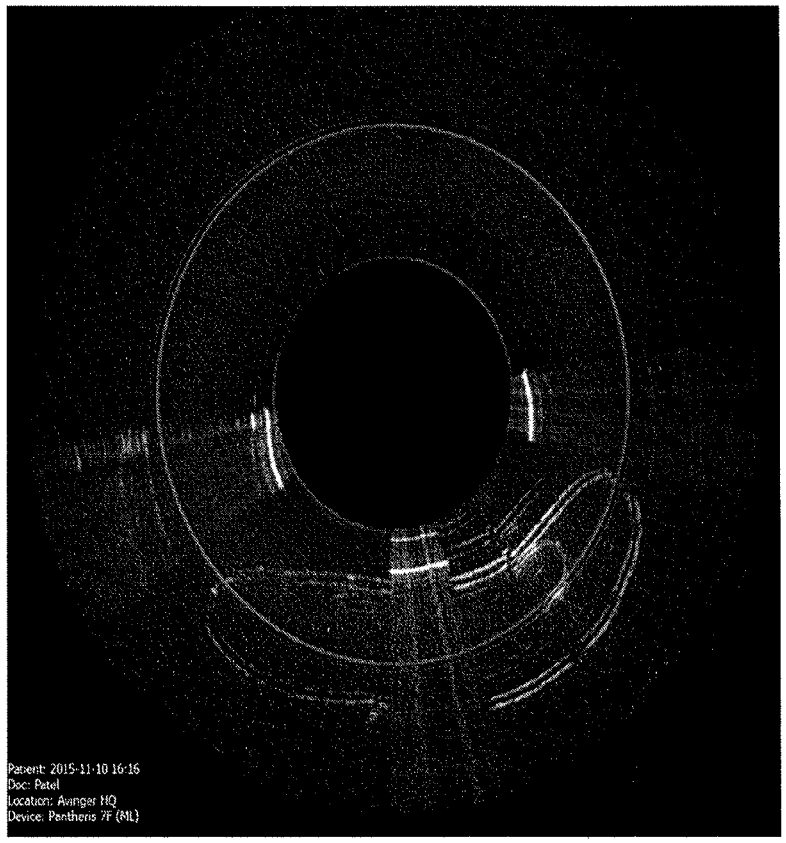
FIG. 5C is an image from an atherectomy catheter that is fully open with correction.

FIGS. 5A-C show the dynamic rotational distortion correction. FIG. 5A shows an OCT image of a vessel as the catheter cutter is being exposed. The cutter is shown at the 12 o'clock position (the inverted horseshoe shaped bright line corresponds to the housing surrounding the cutter while the opening corresponds to the cutter and the area of the vessel imaged). FIGS. 5B and 5C show images taken by the imaging element with correction (FIG. 5C) and without correction (FIG. 5B) when the cutter is fully opened. Without correction, as shown in FIG. 5B, the image has been rotated counter-clockwise about 130 degrees such that the exposed cutter is in the 8 o'clock position. This rotated orientation (caused by rotational lag) can be confusing to the user, given that the actual orientation of the cutter within the vessel has not changed. In contrast, with correction, as shown in FIG. 5C, the cutter has not been rotated relative to its position in FIG. 5A and is still positioned approximately at the 12 o'clock position. Ultimately, being able to see an image of the body lumen with a true orientation will provide the user an intuitive and more efficient way for either imaging or ablative procedures.

Although the controller configured to correct for rotational distortion is described herein as being located within the drive assembly, it is to be appreciated that it could be positioned elsewhere. For example, in one embodiment, a controller on the display can continuously monitor the current and update the sector view accordingly. That is, rather than assuming that every rotation occurs at a constant rotation, the controller could map current draw across each rotation and adjust the pulse gaps according to the current draw.

The methods and systems described herein provide a simple way for correcting rotational lag within an atherectomy catheter or any catheter that includes an imaging system. The rotational lag correction provided for here advantageously corrects the signal prior to an image being displayed. A correction at this stage requires less steps and less complex software programs for correcting the image. Furthermore, the systems and methods described herein provide for continuous monitoring and correction for rotational lag experienced such that the image seen always corresponds to what the imaging fiber is seeing without the need for operator intervention.

In some examples, an analog-to-digital converter may be used to process the information received and transmit the signal information to a processor or microprocessor. Further, signal processing may also include requisite low pass filters as needed. The current changes are indexed and processed to determine a relation between the changes in current and the amount of rotational distortion experienced. Finally, while the present system utilizes changes in current to correlate to an amount of rotational lag experienced, it is also conceivable to use other electrical properties of the system such as changes in voltage, resistance, impedance and so forth, for achieving similar measurements.

The methods and assemblies for correcting rotational lag can be used with a variety of catheters and/or motor assemblies. For example, the methods and assemblies can be used with the atherectomy catheters described in U.S. patent application Ser. No. 15/072,272, filed Mar. 16, 2016, titled "ATHERECTOMY CATHETERS DEVICES HAVING MULTI-CHANNEL BUSHINGS", Publication No. US-2016-0192962-A1 and U.S. patent application Ser. No. 15/076,568, filed Mar. 31, 2016, titled "ATHERECTOMY CATHETERS AND OCCLUSION CROSSING DEVICES", now U.S. Pat. No. 9,498,247 the entireties of which are incorporated by reference herein.

Although described herein as being used with an OCT system, it should be understood that the systems and methods of correcting rotational lag can be used with other types of rotational imaging, such as intravascular ultrasound (IVUS).

In the systems and methods described, there may be programs that are able to continuously, dynamically, and instantaneously correct for rotational lag based upon the current sensed. In some embodiments, the programs are part of a display assembly and/or a drive assembly. In other embodiments, the programs may be controlled in via various telecommunication devices such as laptops, desktops, mobile devices, tablets, and so forth.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter system comprising:
   a catheter body having a driveshaft;
   an imaging sensor fixed relative to a distal end of the driveshaft and configured to rotate therewith;
   a drive motor configured to rotate the driveshaft;
   a sensor configured to measure an amount of current drawn by the drive motor as the driveshaft is rotated;
   a display configured to display one or more images obtained by the imaging sensor as the imaging sensor is rotated; and
   a controller configured to adjust a rotational orientation of the one or more images displayed by the display based upon the measured current.

2. The catheter system of claim 1, wherein the imaging sensor is an optical coherence tomography (OCT) imaging sensor.

3. The catheter system of claim 1, wherein the catheter body further includes a cutter configured to rotate with the driveshaft.

4. The catheter system of claim 3, wherein the imaging sensor is attached to the cutter.

5. The catheter system of claim 1, further comprising a nosecone attached to a distal end of the catheter body and configured to pivot relative thereto.

6. The catheter system of claim 1, wherein the sensor configured to measure the amount of current is a current sense resistor.

7. The catheter system of claim 1, wherein the one or more images are displayed on the display as a sector view.

8. The catheter system of claim 1, wherein adjusting the rotational orientation of the one or more images comprises delaying projection of the one or more images on the display based upon the measured current.

9. The catheter system of claim 1, wherein adjusting a rotational orientation of the one or more images is further based upon a predetermined reference current value and gain value.

10. The catheter system of claim 1, wherein the controller, drive motor, and the sensor configured to measure the amount of current are part of a drive assembly configured to drive the catheter.

11. A catheter drive assembly, comprising:
    a drive motor configured to rotate a driveshaft and imaging sensor of a catheter such that the motor produces a first index pulse;
    a sensor configured to measure an amount of current drawn by the drive motor as the motor produces the first index pulse; and
    a controller configured to:
      determine a second index pulse based upon the measured current and the first index pulse, the second index pulse delayed relative to the first index pulse; and
      send the second index pulse to a display so as to allow display of images gathered by the imaging sensor that are adjusted for rotational lag.

12. The catheter drive assembly of claim 11, wherein the sensor configured to measure the amount of current is a current sense resistor.

13. The catheter drive assembly of claim 11, wherein the controller is configured to determine the second index pulse further based upon a predetermined reference current value and gain value.

14. The catheter drive assembly of claim 11, wherein the imaging sensor is an optical coherence tomography (OCT) imaging sensor.

15. A method of correcting for rotational lag, the method comprising:
- obtaining a reference current value for an imaging catheter when there is no torque on a driveshaft of the catheter;
- measuring an amount of current delivered to a drive motor to rotate the driveshaft during a procedure;
- determining that there has been rotational lag of the driveshaft by determining that the measured amount of current is above the reference current value by a determined amount; and
- correcting a displayed image for the rotational lag based upon the determined amount.

16. The method of claim 15, wherein the measuring, determining, and correcting steps are performed during use of the catheter in an atherectomy procedure.

17. The method of claim 15, wherein correcting a displayed image for the rotational lag based upon the determined amount comprises delaying an index pulse to the displayed image so as to delay projection of the image.

18. The method of claim 15, wherein the imaging catheter is an optical coherence tomography (OCT) imaging catheter, and wherein the displayed image is an OCT image.

19. A method of correcting for rotational lag, the method comprising:
- obtaining a correlation between an amount of rotational distortion in an image and an amount of current drawn by a drive motor of an imaging catheter;
- measuring an amount of current delivered to the drive motor to rotate a driveshaft of the imaging catheter with the drive motor;
- determining that the measured current is above a predetermined value using the correlation to determine a rotational adjustment value; and
- adjusting an orientation of the image based upon the rotational adjustment value.

20. The method of claim 19, wherein the measuring, using, and adjusting steps are performed during use of the catheter in an atherectomy procedure.

21. The method of claim 19, wherein adjusting an orientation of an image comprises delaying an index pulse to a display so as to delay projection of the image on the display.

22. The method of claim 19, wherein the imaging catheter is an optical coherence tomography (OCT) imaging catheter, and wherein the image is an OCT image.

* * * * *